US011406284B2

(12) United States Patent
Malackowski et al.

(10) Patent No.: US 11,406,284 B2
(45) Date of Patent: Aug. 9, 2022

(54) SYSTEM AND METHOD OF CONTROLLING A ROBOTIC SYSTEM FOR MANIPULATING ANATOMY OF A PATIENT DURING A SURGICAL PROCEDURE

(71) Applicant: Stryker Corporation, Kalamazoo, MI (US)

(72) Inventors: Donald W. Malackowski, Schoolcraft, MI (US); Douglas A. Staunton, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 464 days.

(21) Appl. No.: 16/508,790

(22) Filed: Jul. 11, 2019

(65) Prior Publication Data

US 2019/0336043 A1 Nov. 7, 2019

Related U.S. Application Data

(63) Continuation of application No. 14/500,280, filed on Sep. 29, 2014, now Pat. No. 10,390,737.

(Continued)

(51) Int. Cl.
*A61B 5/11* (2006.01)
*A61B 34/30* (2016.01)
(Continued)

(52) U.S. Cl.
CPC .......... *A61B 5/1114* (2013.01); *A61B 5/0036* (2018.08); *A61B 5/4504* (2013.01);
(Continued)

(58) Field of Classification Search
CPC .......... A61B 17/025; A61B 2017/0256; A61B 2017/0268; A61B 2017/0275;
(Continued)

(56) References Cited

U.S. PATENT DOCUMENTS 5,339,799 A 8/1994 Kami et al.
5,368,044 A 11/1994 Cain et al.
(Continued)

FOREIGN PATENT DOCUMENTS

JP H04231034 A 8/1992
JP 2004350781 A 12/2004
(Continued)

OTHER PUBLICATIONS

"Robot." Merriam-Webster.com Dictionary, Merriam-Webster, https://www.merriam-webster.com/dictionary/robot. Accessed Nov. 27, 2021.*
(Continued)

*Primary Examiner* — Thomas McEvoy
(74) *Attorney, Agent, or Firm* — Howard & Howard Attorneys PLLC

(57) ABSTRACT

System and methods of controlling a robotic system are disclosed. The robotic system interacts with an anatomy that is held by a support. The robotic system comprises a force-applying device that applies a force externally to the anatomy while the anatomy is held by the support. A controller measures the extent to which the anatomy is held by the support and controls the robotic system based on the measured extent.

19 Claims, 5 Drawing Sheets

Related U.S. Application Data

(60) Provisional application No. 61/884,500, filed on Sep. 30, 2013.

(51) Int. Cl.
  *A61B 34/32* (2016.01)
  *A61B 5/00* (2006.01)
  *A61B 17/16* (2006.01)
  *A61B 34/20* (2016.01)
  *A61B 90/00* (2016.01)
  *A61G 13/06* (2006.01)
  *A61G 13/10* (2006.01)

(52) U.S. Cl.
  CPC .............. *A61B 5/742* (2013.01); *A61B 17/16* (2013.01); *A61B 34/30* (2016.02); *A61B 34/32* (2016.02); *A61B 2034/2055* (2016.02); *A61B 2090/064* (2016.02); *A61B 2090/065* (2016.02); *A61G 13/06* (2013.01); *A61G 13/101* (2013.01)

(58) Field of Classification Search
  CPC ....... A61B 5/1114; A61B 34/30; A61B 34/32; A61B 2090/064; A61G 13/1235; A61G 13/124; A61G 13/1245; A61G 13/125; A61G 2203/32; A61G 2203/34; A61G 2203/36; A61G 2203/38; A61G 2203/40; A61G 2203/78
  See application file for complete search history.

(56) References Cited

U.S. PATENT DOCUMENTS

| | | | |
|---|---|---|---|
| 5,408,409 A | 4/1995 | Glassman et al. | |
| 7,206,626 B2 | 4/2007 | Quaid, III | |
| 7,206,627 B2 | 4/2007 | Abovitz et al. | |
| 7,747,311 B2 | 6/2010 | Quaid, III | |
| 7,831,292 B2 | 11/2010 | Quaid et al. | |
| 8,010,180 B2 | 8/2011 | Quaid et al. | |
| 8,095,200 B2 | 1/2012 | Quaid, III | |
| 8,391,954 B2 | 3/2013 | Quaid, III | |
| 9,008,757 B2 | 4/2015 | Wu | |
| 9,119,655 B2 | 9/2015 | Bowling et al. | |
| 9,271,804 B2 | 3/2016 | Wu | |
| 9,274,014 B2 | 3/2016 | Janik et al. | |
| 9,615,987 B2 | 4/2017 | Worm et al. | |
| 9,724,165 B2 | 8/2017 | Arata et al. | |
| 2004/0034282 A1 | 2/2004 | Quaid | |
| 2004/0106916 A1 | 6/2004 | Quaid et al. | |
| 2006/0142657 A1 | 6/2006 | Quaid et al. | |
| 2007/0169267 A1* | 7/2007 | Paz ....................... A61G 7/053 5/610 |
| 2009/0012532 A1 | 1/2009 | Quaid et al. | |
| 2009/0149867 A1 | 6/2009 | Glozman et al. | |
| 2011/0112549 A1 | 5/2011 | Bach et al. | |
| 2011/0301500 A1 | 12/2011 | Maguire et al. | |
| 2011/0306985 A1 | 12/2011 | Inoue et al. | |
| 2012/0016230 A1 | 1/2012 | Kishima et al. | |
| 2012/0109150 A1 | 5/2012 | Quaid et al. | |
| 2012/0109152 A1 | 5/2012 | Quaid, III | |
| 2013/0019883 A1 | 1/2013 | Worm et al. | |
| 2013/0197543 A1 | 8/2013 | Bonutti | |
| 2013/0340169 A1* | 12/2013 | Zerhusen ............... A61G 7/008 5/617 |
| 2015/0094736 A1 | 4/2015 | Malackowski et al. | |

FOREIGN PATENT DOCUMENTS

| | | |
|---|---|---|
| JP | 2007202950 A | 8/2007 |
| JP | 2008538184 A | 10/2008 |
| JP | 2009537230 A | 10/2009 |
| JP | 2012023492 A | 2/2012 |
| WO | 2006091494 A1 | 8/2006 |

OTHER PUBLICATIONS

English language abstract for JP 2012-023492 A extracted from espacenet.com database on May 10, 2021, 2 pages.

Dec. 12, 2014 International Search Report for PCT/US2014/058225.

D.J. Dunn, Solid Mechanics Dynamics Tutorial—Damped Vibrations, 1-13, published before Sep. 30, 2013; 13 pages.

English language abstract for JP 2008-538184 extracted from espacenet.com database on Jul. 11, 2018, 2 pages.

English language abstract for JP 2009-537230 extracted from espacenet.com database on Jul. 11, 2018, 2 pages.

English language abstract for JPH 04-231034 extracted from espacenet.com database on Jan. 27, 2020, 2 pages.

English language abstract and machine-assisted English translation for JP 2004-350781 extracted from espacenet.com database on Dec. 9, 2020, 8 pages.

English language abstract and machine-assisted English translation for JP 2007-202950 A extracted from espacenet.com database on Jun. 2, 2022, 9 pages.

* cited by examiner

SYSTEM AND METHOD OF CONTROLLING A ROBOTIC SYSTEM FOR MANIPULATING ANATOMY OF A PATIENT DURING A SURGICAL PROCEDURE

CROSS-REFERENCE TO RELATED APPLICATIONS

The subject patent application is a continuation of U.S. Non-Provisional patent application Ser. No. 14/500,280, filed Sep. 29, 2014, which claims priority to and all the benefits of U.S. Provisional Patent Application No. 61/884,500 filed on Sep. 30, 2013, which is incorporated herein by reference.

TECHNICAL FIELD

The present disclosure relates generally to systems and methods of controlling a robotic system used during a surgical procedure to treat a patient's anatomy. More specifically, one aspect of the present invention relates to controlling the robotic system based on a response of the anatomy to a force exerted on the anatomy.

BACKGROUND

Medical personnel, such as practitioners, have recently found benefit in using robotic systems to perform surgical procedures. Such a robotic system typically includes a moveable arm. The movable arm has a free, distal end that can be positioned with a very high degree of accuracy. A surgical instrument is attached to the free end of the arm. The surgical instrument is designed to be applied to a surgical site.

In early robotic systems, medical personnel rigidly fixed the patient in a surgical holder thereby fixing the surgical site in a static patient coordinate system. However, recent robotic systems employ surgical holders that allow slight movements of the patient. As such, modern surgical holders do not rigidly fix the surgical site in a static patient coordinate system.

One drawback of allowing movement of the surgical site is the possibility that the surgical site is too loosely secured during autonomous operation of the robotic system. In this situation, a position control loop of the robotic system continually attempts to reach a target at the surgical site while at the same time constantly pushing the target out of reach. As a result, the surgical instrument is positioned inaccurately at the surgical site, thereby adding unnecessary delay to the surgical procedure.

As such, it is desirable to develop a robotic system which can compensate for these conditions or prevent the condition altogether.

SUMMARY

In one embodiment, a robotic system is provided which is configured to interact with an anatomy held by a support. The robotic system comprises a force-applying device configured to apply a force externally to the anatomy held by the support. A controller is configured to measure an extent to which the anatomy is held by the support and to control the robotic system based on the measured extent.

In one embodiment, a method of operating a robotic system is provided. The robotic system is configured to interact with an anatomy held by a support. The robotic system comprises a force-applying device and a controller. The method comprises applying, with the force-applying device, a force externally to the anatomy held by the support. A controller measures an extent to which the anatomy is held by the support and controls the robotic system based on the measured extent.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
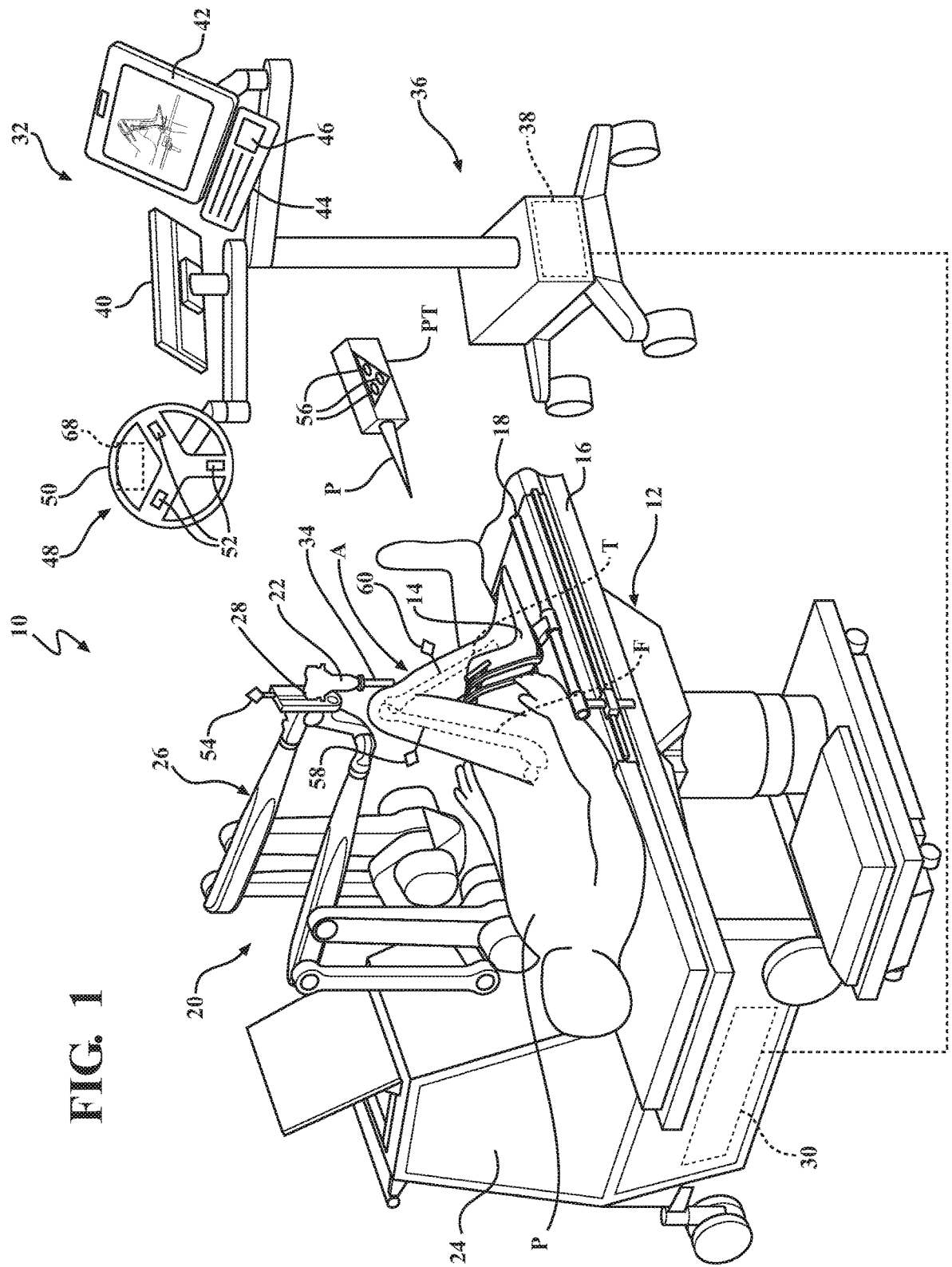
FIG. 1 is a perspective view of a robotic system.

Systems and methods are disclosed for controlling a robotic system to perform a surgical procedure. Referring to FIG. 1, a robotic system 10 for performing the surgical procedure on a patient is shown.

Prior to the surgical procedure, medical personnel may collect preoperative data of the patient. Preoperative data may come from an x-ray, a CT scan, a MRI or any other modality that can collect preoperative data. The collected preoperative data may be saved and stored for use by the robotic system 10.

In one embodiment, the patient is placed onto a support station 12 during the surgical procedure. The support station 12 has a support or surgical holder 14 that secures anatomy of the patient. The anatomy of the patient is identified by reference to A in FIG. 1. The anatomy may be a femur F and/or a tibia T in some embodiments. It should be appreciated that the surgical holder 14 may be coupled to the support station 12 in any fashion.

In FIG. 1, the support station 12 includes an operating table 16 having a track 18. The surgical holder 14 is coupled to the track 18 such that the surgical holder 14 may move along the track 18 on the table 16. During the surgical procedure, medical personnel may slide the surgical holder 14 forward and backward along the track 18 to position the anatomy. The surgical holder 14 may lock in the track 18 such that the surgical holder 14 is in a fixed position. For example, the surgical holder 14 may lock in the fixed position when the anatomy is in an optimal position. One embodiment of a suitable surgical holder 14 is shown in U.S. patent application Ser. No. 13/554,010 filed Jul. 20, 2012 entitled "Multi-Position Limb Holder," which is hereby incorporated by reference herein in its entirety.

Although the surgical holder 14 may be in the fixed position, the anatomy is placed in the surgical holder 14 such that the anatomy may still move relative to the surgical holder 14. For example, the anatomy may move relative to the surgical holder 14 in one or more degrees of freedom, including up to six degrees of freedom. In turn, the anatomy is effectively a dynamic member of the robotic system 10. Still, the surgical holder 14 is configured to securely hold the anatomy in a manner that limits gross or major movements of the anatomy upon the application of force to the anatomy so that the robotic system 10 is able to treat the anatomy.

The robotic system 10 includes a manipulator 20 that may be used to manipulate a surgical instrument 22 to treat the anatomy. One embodiment of the manipulator 20 is described in U.S. Pat. No. 9,119,655, entitled "Surgical Manipulator Capable of Controlling a Surgical Instrument in Multiple Modes," which is hereby incorporated by reference herein in its entirety.

The manipulator 20 includes a cart 24 and a pair of arms 26 extending from the cart 24 to a distal end. The instrument 22 is coupled to the distal end of the pair of arms 26. It should be appreciated that the instrument 22 may be integrated with the manipulator 20 in any fashion. In one embodiment, the instrument 22 includes an energy applicator 34 extending from the instrument 22. The energy applicator 34 may be an ultrasonic tip, bur, or any other treatment device for performing a surgical procedure. The surgical holder 14 is generally fixed relative to the manipulator 20.

The manipulator 20 and the instrument 22 may also have one or more sensors and/or encoders for sensing position, force/torque, etc. The sensors and encoders may be of any form to those known in the art to provide physical data or other types of data associated with the manipulator 20 and the instrument 22. One type of sensor is a force/torque sensor 28, which can detect forces and torques applied to the instrument 22. One embodiment of a suitable force/torque sensor 28 is shown in U.S. patent application Ser. No. 14/199,299, filed Mar. 6, 2014, entitled "Sensor Assembly and Method for Measuring Forces and Torques", which is hereby incorporated by reference herein in its entirety.

The manipulator 20 also includes a manipulator controller 30. The manipulator controller 30 communicates with the sensors and encoders, including the force/torque sensor 28. The manipulator controller 30 is able to communicate with the force/torque sensor 28 such that the forces and torques sensed by the force/torque sensor 28 are communicated back to the manipulator controller 30. The manipulator controller 30 further communicates with a navigation system 32.

The robotic system 10, and more specifically, the manipulator 20, may be operated manually or autonomously. When operated manually, the robotic system 10 is operating in a manual mode. In the manual mode, medical personnel can manually position the instrument 22 by applying commands to the robotic system 10. One example of applying commands includes the medical personnel grasping and applying forces/torques to the instrument 22. Based on the commands applied by the medical personnel, the robotic system 10 actuates the arms 26 to cause corresponding and effectively simultaneous, real time, movement of the instrument 22 to the desired position.

The robotic system 10 is configured to autonomously control the instrument 22. More specifically, the robotic system 10 autonomously controls the instrument 22 in an autonomous mode or a semi-autonomous mode of operation. In the autonomous or semi-autonomous modes, the manipulator controller 30 processes preloaded data, data from the navigation system 32 and data from the encoders to derive a path along which the instrument 22 will follow. The path may be preprogrammed or predetermined. The robotic system 10 actuates the arms 26 to cause autonomous movement of the instrument 22 along the path to treat the anatomy. The robotic system 10 performs the procedure with effectively no input from the medical personnel.

In the semi-autonomous mode, the robotic system 10 autonomously moves the instrument 22 along the path. However, medical personnel are able to assert commands to control the operation of the robotic system 10. For example, the robotic system 10 may require that the medical personnel continually depress a control button or switch associated with the robotic system 10 to permit movement of the instrument. Upon the release of the button or switch by the medical personnel, the advancement of the instrument 22 temporarily halts. One suitable navigation system utilized in the autonomous or semi-autonomous mode is described in U.S. application Ser. No. 14/035,207 filed on Sep. 24, 2013, entitled "Navigation System Including Optical and Non-Optical Sensors," which is hereby incorporated by reference herein its entirety. However, one should appreciate that other navigation systems may be used.

The navigation system 32 may include a computer cart assembly 36 that houses a navigation computer 38. A navigation interface is in operative communication with the navigation computer 38. The navigation interface allows the medical personnel to communicate with the robotic system 10. The navigation interface includes at least one display 40, 42, and input devices 44, 46 such as a keyboard and a mouse, to allow the medical personnel to communicate with the navigation computer 38.

The navigation computer 38 cooperates with the manipulator controller 30 to control the manipulator 20. The navigation computer 38 provides pose data of the instrument 22 to the manipulator controller 30 such that the manipulator controller 30 may direct motion of the manipulator 20, and in turn, the instrument 22.

A localizer 48 communicates with the navigation computer 38. In the embodiment shown in FIG. 1, the localizer 48 is an optical localizer 48 and includes a camera unit 50. The camera unit 50 has an outer casing that houses one or more optical sensors 52. In some embodiments, at least two optical sensors 52 are employed. In other embodiments, three or more optical sensors 52 may be used.

The navigation system 32 includes one or more trackers. The trackers may include a pointer tracker PT, an instrument tracker 54, a first patient tracker 58, and a second patient tracker 60. The trackers include active markers 56. The active markers 56 may be light emitting diodes or LEDs. In other embodiments, the trackers 54, 58, 60 may have passive markers, such as reflectors that reflect light emitted from the camera unit 50. It should be appreciated that additional trackers may be incorporated into the navigation system 32 to track additional components that may be part of the robotic system 10.

In the illustrated embodiment of FIG. 1, the first patient tracker 58 is firmly affixed to the femur F of the patient P and the second patient tracker 60 is firmly affixed to the tibia T of the patient P. The patient trackers 58, 60 are firmly affixed to sections of bone. In addition, the instrument tracker 54 is firmly attached to the instrument 22. The trackers 54, 58, 60 may be fixed to their respective components in any manner which one may find useful.

Figure 2:
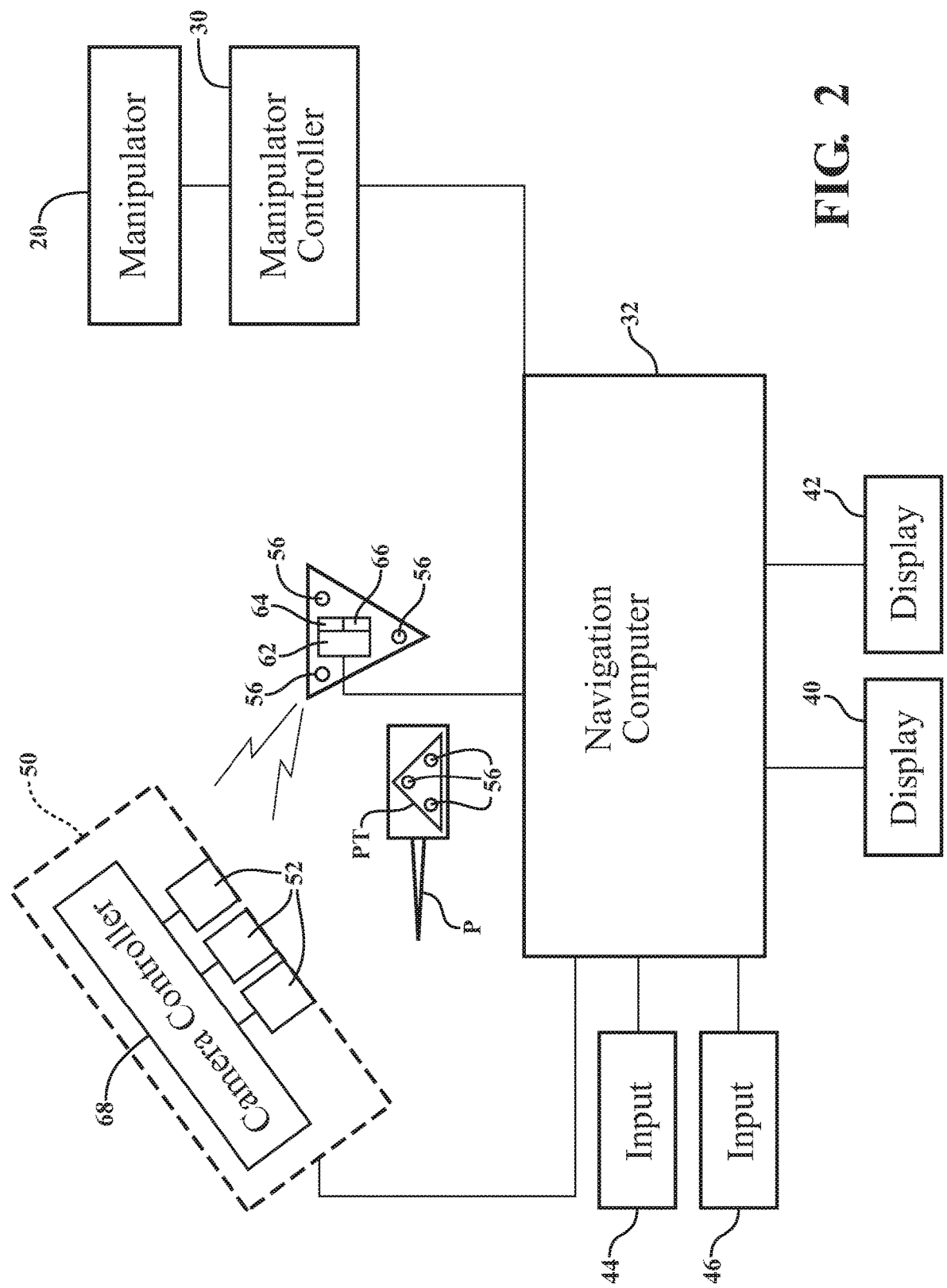
FIG. 2 is a schematic view of the robotic system.

Referring to FIG. 2, each of the LEDs are connected to a tracker controller 62 located in a housing (not shown) of the associated tracker that transmits/receives data to/from the navigation computer 38. The trackers 54, 58, 60 also include a 3-dimensional gyroscope sensor 64 that measures angular velocities of the trackers 54, 58, 60. The trackers 54, 58, 60 also include an accelerometer 66 to measure acceleration in the x, y, and z coordinate system.

The camera unit 50 includes a camera controller 68 in communication with the optical sensors 52 to communicate pose data from the active markers 56 of the trackers 54, 58, 60. The camera controller 68 then communicates the pose data to the navigation computer 38. The navigation computer 38 then processes the pose data with additional preoperative data, to communicate the pose of the instrument 22 and thus the energy applicator 34 in relationship to the anatomy of the patient. In one embodiment, the navigation interface communicates such data to the medical personnel. It should be appreciated that one of ordinary skill in the art may find other methods not described in the previous embodiments for the medical personnel to communicate with the robotic system 10.

During a surgical procedure, it is desirable for the robotic system 10 to switch from the manual mode to the semi-autonomous or autonomous mode. In some procedures, such as bone cutting procedures, it is desirable for the anatomy to be securely located in the surgical holder 14 such that the anatomy does not move at the same rate as the instrument 22 when the instrument 22 engages the bone. Otherwise, the instrument 22 will be unable to cut any bone. In other words, it is desirable for the anatomy to have a certain minimum stiffness or other characteristic when secured in the surgical holder 14. Additionally, there is a desire to control the robotic system 10 based on the value of certain characteristics, such as stiffness, to ensure that the anatomy moves at a lower rate than the instrument 22 when the instrument 22 is applied to the anatomy during the surgical procedure.

To account for movement of the anatomy as the instrument 22 is applied to the anatomy, the robotic system 10 is calibrated based on one or more characteristics of the anatomy. The one or more characteristics may be a stiffness characteristic (k), a damping characteristic (b), a mass (m), a damping ratio ($\zeta$), a frequency response ($\omega n$) and/or other characteristic. The stiffness characteristic (k) may be further defined as a spring constant. In another example, the characteristic includes data representing the extent to which the anatomy is secured by the surgical holder 14. More specifically, the characteristic includes data representing the extent to which the anatomy moves relative to the surgical holder 14.

Figure 3:
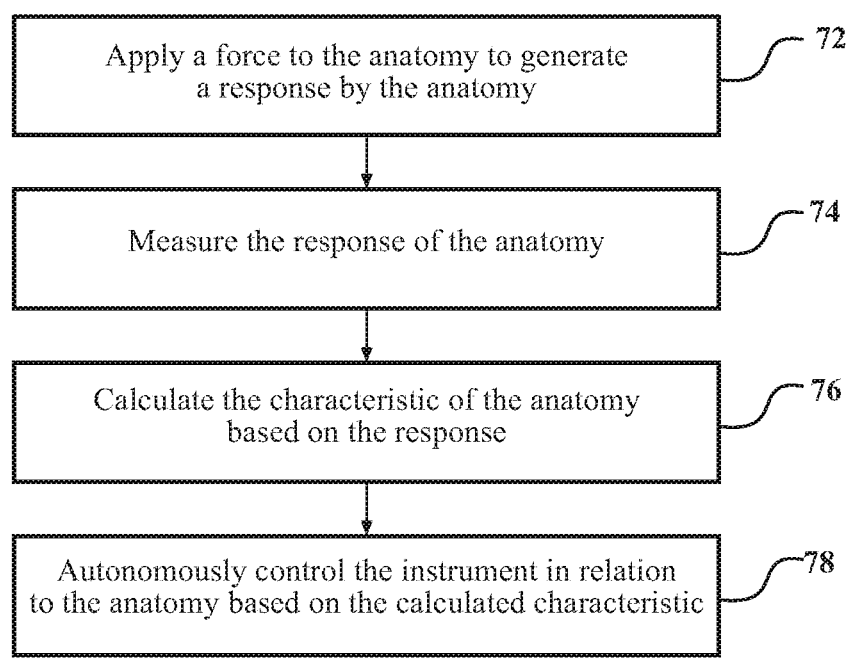
FIG. 3 is a flow chart of a method for controlling the robotic system.

FIG. 3 illustrates the basic steps of controlling the robotic system 10 for manipulating the anatomy of the patient P during the surgical procedure. A force is applied to the anatomy to generate a response by the anatomy in step 72. The response of the anatomy is measured in step 74. In step 76, the characteristic of the anatomy is calculated based on the response. In step 78, the instrument 22 is autonomously controlled in relation to the anatomy based on the calculated characteristic.

In order to apply the force to the anatomy at step 72, a force-applying device is generally positioned adjacent to or against the anatomy. In one embodiment, the robotic system 10, and more specifically, the manipulator controller 30, actively moves the force-applying device toward the anatomy to apply the force. Alternatively, the robotic system 10 may be stationary and the force-applying device extends from the robotic system 10 toward the anatomy to apply the force. Such movement of the force-applying device may be made independent of the manipulator controller 30. The force-applying device may have any suitable configuration. For example, the instrument 22 that manipulates the anatomy is the force-applying device. In another example, a device other than the instrument 22, such as a sensor or gauge, acts as the force-applying device and is positioned against the anatomy. Any suitable device other than the instrument 22 may act as the force-applying device.

The medical personnel may provide input in the manual mode so that the robotic system 10, and more specifically, the manipulator controller 30 positions the instrument 22, or other force-applying device, against the anatomy. In some cases, the energy applicator 34 may be positioned against the anatomy. In other cases, the surgical instrument 22 is outfitted with a calibration probe (not shown) that has a non-invasive and biocompatible structure at its distal end to position against the anatomy.

In alternative versions, the robotic system 10 may be utilized in the semi-autonomous or autonomous modes to autonomously position the instrument 22 against the anatomy prior to applying the force in step 72. The medical personnel may interact with the navigation interface to intervene during autonomous operation to direct positioning of the instrument 22 against the anatomy. It should be appreciated that the medical personnel may interact with the manipulator 20, navigation system 32, or any other component of the robotic system 10 in any way that one of ordinary skill in the art would find it useful to direct the position of the instrument 22. Additionally, the medical personnel may switch between manual, autonomous, and/or semi-autonomous modes when positioning the instrument 22 against the anatomy.

The force is applied to the anatomy in step 72. In one embodiment of step 72, the instrument 22 applies the force to the anatomy. In another embodiment, the force—applying device other than the instrument 22 applies the force to the anatomy. In either instance, the force may be applied to the anatomy in the manual mode, autonomous mode and/or semi-autonomous mode. In one embodiment, the force is predetermined. Furthermore, the force may be applied in one degree of freedom. Alternatively, forces and torques may be applied in several degrees of freedom, such as six degrees of freedom.

In one embodiment, the force is applied to the anatomy according to a step function. In such instances, the force is applied at first level during a first interval and at a second level during a second interval that is consecutive to the first interval. The first level may be higher than the second level, or vice-versa. As such, the robotic system 10 may apply forces of various levels to the anatomy. The step function may include any suitable number of levels and intervals.

In another embodiment, the force is applied to the anatomy according to an impulse function F(t). In this embodiment, the force is applied to the anatomy and a signal is recorded to measure the reaction of the anatomy as a function of time.

In yet another embodiment, step 72 includes activating a calibration procedure. As such, applying the force to the anatomy occurs in response to activation of the calibration procedure. The calibration procedure may be a stored calibration program in the manipulator controller 30. The stored calibration program may be stored in any medium that can store a computer program and is a part of the robotic system 10. The navigation interface may prompt a user to start the calibration procedure. Alternatively, the calibration procedure may start automatically.

During the calibration procedure, the stored calibration program can cooperate with the manipulator controller 30 to instruct the instrument 22 to apply the force to the anatomy. In one embodiment, the force is applied to the anatomy such that that the instrument 22 maintains contact with the anatomy throughout the calibration procedure. Additionally or alternatively, the manipulator 20 may continue to increase force applied to the anatomy until a predetermined threshold force is reached.

The anatomy generates the response after the force is applied. As will be described in detail below, the generated response of the anatomy may take any combination of various forms. In one embodiment, the generated response of the anatomy is a mechanical response. For example, the generated response may be mechanical movement of the anatomy, or more specifically, displacement or rotational movement of the anatomy. Those skilled in the art will appreciate that the generated response of the anatomy may take non-mechanical forms. For example, the generated response may be an electrical response.

After the response by the anatomy is generated, the response is measured at step 74. The response may be measured according to various methods. A response-measuring device measures the response. In one embodiment of step 74, the response is measured using a force/torque sensor 28. The force/torque sensor 28 may be associated with the instrument 22. When the instrument 22 applies forces and/or torques to the anatomy, the force/torque sensor 28 may measure the forces and/or torques. Alternatively, the force/torque sensor 28 may be associated with a device other than the instrument 22. The forces and/or torques may be measured as a function of time. In addition, the forces and/or torques may be measured discretely or continuously.

In another embodiment of step 74, the response of the anatomy is measured by measuring a joint torque. The joint torque corresponds to the torque related to one of the joints of the manipulator 20. Any suitable sensors and/or encoders may sense the joint torque. Additionally, more than one joint torque may be measured. In one embodiment, the joint torques are calculated and converted into tool center point (TCP) forces/torques using equation (1) below. In equation (1), (J') is the transpose of the Jacobian from the TCP to the joints and (t) is the vector of the joint torques. The joint torque may be calculated from the current drawn by motor controllers used to manipulate the instrument 22, as shown in formula (2) below, where (kt) is the motor torque constant and (i) is the current. Additionally, an estimate of the joint torques may be determined using joint torque sensors. The joint torques may be measured according to various other methods.

$$F = J'^{*}t \quad (1)$$

$$\tau = kt^{*}t \quad (2)$$

In yet another embodiment of step 74, the response of the anatomy is measured by measuring a displacement of the anatomy. The displacement may be the distance that the anatomy moves because of having the force applied thereto. The displacement may be measured as a function of time. In addition, the displacement may be measured discretely or continuously. In some embodiments, the manipulator 20 may continue to apply the instrument 22 to the anatomy until a desired displacement is reached. Any suitable device or method may be utilized to measure the displacement of the anatomy. In one example, the navigation system 32 calculates the displacement by measuring changes in position of the trackers 58 and 60. For instance, the navigation system 32 may determine an initial position of the anatomy prior to applying the force at step 72. After the force is applied, the navigation system 32 may determine a displaced position of the anatomy. The navigation system 32 may then compare the displaced position relative to the initial position to determine the displacement.

When measuring the displacement, the robotic system 10 may record a final force and displacement measurement. In step 74, the manipulator 20 may wait a defined settling time so that the anatomy and the instrument 22 reach an equilibrium point before the robotic system 10 records the final force and displacement measurement. Additionally, the manipulator controller 30 may calculate the displacement of the anatomy using the encoders and kinematic calculations. It should be appreciated that one of ordinary skill in the art may find alternative methods to calculate the displacement of the anatomy.

In measuring the response of the anatomy, the mass (m) of the anatomy may be considered. In one embodiment, the mass of the anatomy is estimated from the preoperative data. Additionally, the mass of the anatomy may be added to the mass of the surgical holder 14. As such, the mass of the anatomy and the holder 14 may be considered in measuring the response of the anatomy. Furthermore, both the mass and the displacement may be taken into account when measuring the response.

The response of the anatomy may be measured according any combination of the aforementioned embodiments. In one embodiment, certain steps of the method occur at different times. For example, steps 72 and 74 occur at different times. More specifically, the force is applied to the anatomy before the response of the anatomy is measured. In another example, steps 72 and 78 occur at different times. Specifically, the force is applied to the anatomy prior to autonomous control of the instrument 22. In such instances, the step 72 of applying the force to the anatomy occurs separately and distinctly from the step 78 of autonomously controlling the instrument 22.

Alternatively, certain steps of the method may occur at the same time. For example, steps 72 and 74 may occur simultaneously such that the response of the anatomy is measured contemporaneously as the force is applied. In another example, step 72 occurs at the same time as step 78. Specifically, the force is applied as the instrument 22 is autonomously controlled. In such instances, the step 72 of applying the force need not be executed prior to autonomously controlling the instrument 22. That is, autonomous control of the instrument 22 may be initiated without having previously applied the force to the anatomy. Rather, during autonomous control of the instrument 22, the force is continuously applied to the anatomy. Additionally, steps 74 and 76 may occur at the same time as step 78. That is, the response of the anatomy may be measured and the characteristic of the anatomy may be calculated as the instrument 22 is autonomously controlled.

Additionally, it should be appreciated that one of ordinary skill in the art may find alternative methods of measuring the response of the anatomy without departing from the broadest scope of the method.

As described above, the characteristic of the anatomy is calculated based on the measured response of the anatomy at step 76. The characteristic may be calculated according to various embodiments. In one embodiment, the characteristic is measured using a static approach. In this approach, a stiffness characteristic (k) of the anatomy is determined. The force applied to the anatomy is known and is represented by (F). The calculated displacement of the anatomy is also known and is represented by (x). The manipulator controller 30 processes the force (F) and the calculated displacement (x) by inputting the force (F) and the displacement (x) into equation (3) below, to solve for the stiffness characteristic (k) in step 76.

$$F = k^{*}x \quad (3)$$

In equation (3), the static deflection of the anatomy is measured. The stiffness characteristic (k) is the spring constant, which may be estimated under steady state conditions. It should be appreciated that one of ordinary skill in the art may find alternative static approaches for calculating the characteristic of the anatomy.

In another embodiment, the characteristic is measured using a dynamic approach. In this approach, a step or impulse response of the anatomy is measured. Parameters are estimated using the following characteristic equation (4) for a mass/spring/damper model:

$$m*x''+b*x'+k*x=0 \quad (4)$$

In equation (4), (m) is the mass of the holder and/or anatomy, (b) is a damping characteristic, such as a damping coefficient, (k) is the spring constant, (x") is the second derivative with respect to time of displacement (e.g., acceleration), (x') is the first derivative with respect to time of displacement (e.g., velocity), and (x) is displacement. In equation (4), at least one of the parameters (m, b, or k) may be assumed or known to allow for easy estimation of the remaining parameters. For example, if two of the three parameters are known, this allows for an improved estimation of the third parameter. In one example, the mass is known or may be estimated from available clinical data. In another example, the spring constant (k) is computed and estimated through a static test. In either example, the remaining two variables may be calculated from the experimental data. Alternatively, the approach of both examples can be combined to provide for initial estimates for both (m) and (k) such that the damping characteristic (b) can be calculated from the experimental data.

In another embodiment of step 76, calculating the characteristic includes estimating the resonant frequency ($\omega m$) and the damping ratio ($\zeta$) of the anatomy's response from a displacement over time graph generated by the manipulator controller 30. Using the estimated mass, and solving equation (5) and equation (6) below, the stiffness characteristic (k) and the damping characteristic (b) can be calculated. In other examples, the mass, the stiffness characteristic (k), and the damping characteristic (b) are estimated.

$$\omega n = \sqrt{k/m} \quad (5)$$

$$(2*(\zeta)*\omega n) = \frac{b}{m} \quad (6)$$

In yet another embodiment, step 76 includes performing an iterative optimization routine to search for parameter values that minimize the mean square error between a calculated response, xc(t), and an experimental response x(t), as evaluated from the displacement versus time data. In this embodiment, the full transfer function for the mass, spring, damper model, H(s) in equation (7), is utilized to calculate the value of the mass (m), the damping characteristic (b) and the stiffness characteristic (k).

$$H(s) = \frac{X(s)}{F(s)} = 1/(m*s^2+b*s+k) \quad (7)$$

In equation (8), a force input, f(t), is known and the Laplace transform of f(t) is calculated to solve for F(s). As such, F(s) in equation (7) is the Laplace transform of the force input. In equation (7), X(s) is the Laplace transform of a translation output, and s is the Laplace frequency variable. In equation (7), X(s) is solved using the calculated values of F(s) and the guessed values of (m), (k), and (b). Once X(s) is known, the inverse Laplace transform, as shown by equation (9) below, is used to convert X(s) from the frequency domain to the time domain as xc(t). The mean square error is then calculated between xc(t) and x(t). The process is then repeated by using updated guesses for (m), (k), and (b) until the mean square error converges within an acceptable margin.

$$F(s)=\mathcal{L}\{f(t)\}(s) \quad (8)$$

$$xc(t)=\mathcal{L}^{-1}\{X(s)\} \quad (9)$$

It should be appreciated that one of ordinary skill in the art could anticipate using alternative mathematical methods not stated above to calculate the characteristic of the anatomy.

As described, at step 78 the robotic system 10 autonomously controls the instrument 22 in relation to the anatomy based on the calculated characteristic. By doing so, the method takes the characteristic of the anatomy into account when autonomously controlling the instrument 22. The manipulator controller 30 may control the placement of the instrument 22, and in turn, the tip of the energy applicator 34 in relationship to the anatomy based on the calculated characteristic. According to one embodiment, autonomously controlling the instrument 22 includes utilizing the calculated characteristic to account for movement of the anatomy during the surgical procedure.

In another embodiment, the calculated characteristic is used as a factor in controlling a feed rate of the manipulator in the autonomous or semi-autonomous modes. The feed rate of the manipulator is described in U.S. Pat. No. 9,119, 655, entitled "Surgical Manipulator Capable of Controlling a Surgical Instrument in Multiple Modes," which is hereby incorporated by reference herein in its entirety.

In one example, the feed rate of the instrument 22 is adjusted based on the calculated characteristic. For example, the feed rate is adjusted such that the feed rate is faster than a rate at which the anatomy moves as the instrument 22 is applied to the anatomy during the surgical procedure. This way, the calculated characteristic is factored in to ensure that the feed rate of the instrument 22 is sufficient to allow the instrument 22 to contact anatomy that may be susceptible to movement in the surgical holder 14.

In another example, feed rate is adjusted based on data representing the extent to which the anatomy is secured by the surgical holder 14. More specifically, the feed rate is adjusted based on data representing the extent to which the anatomy moves relative to the surgical holder 14. Such data may be derived by comparing an actual position of the instrument 22 to an intended position of the instrument 22 relative to the anatomy. The navigation system 32 tracks the anatomy and the instrument 22 to determine the actual position. The actual position may include a traversed cut path of the instrument 22. The intended position may be predetermined and preloaded data representing an intended traversed cut path. The cut path of the instrument 22 may be determined at a plurality of discrete points. A profile error can be determined between the actual path and the intended path. The profile error may then be compared to a predetermined threshold. In one example, if the percentage of traversed cut path points having a profile error exceeding the threshold is deemed unacceptable, the feed rate is reduced and/or a notification is displayed. In some cases, the profile error target as well as the acceptable percentage could be adjusted or variable. Such an adjustment may be made, for example, depending on whether the cut is a rough or finish cut. Additionally, such an adjustment may be made based on criticality of the anatomy being cut. Undercuts may also have a different threshold than overcuts. In another example, the method described above is employed to compare actual bone removal by the instrument 22 to intended bone removal by the instrument 22.

In another embodiment, autonomously controlling the instrument includes setting a maximum feed rate of the instrument 22 based on the calculated characteristic of the anatomy. In some instances, the robotic system 10 may designate a default maximum feed rate of the instrument 22 depending on the specific anatomy that is subject to the surgical procedure. In other words, the default maximum feed rate may be different depending upon the subject anatomy. However, depending upon the calculated characteristic, the robotic system 10 may set the maximum feed rate at or below the default maximum feed rate. For example, if the calculated characteristic indicates a relatively stiff anatomy, then the robotic system 10 may set the maximum feed rate at the default maximum feed rate. The robotic system 10 may maintain the maximum feed rate because there is less chance for inaccuracy in application of the instrument 22 when the anatomy is relatively stiff. Alternatively, for example, if the calculated characteristic indicates a relatively loosely secured anatomy, then the robotic system 10 may set the maximum feed rate of the instrument 22 below the default maximum feed rate or within a range of feed rates that are below the default maximum feed rate. The robotic system 10 may limit the maximum feed rate to counteract inaccuracies in application of the instrument 22 that may result from the anatomy being loosely secured. In other embodiments, the maximum feed rate is set simply as a function of the calculated characteristic notwithstanding a default maximum feed rate as described above.

In addition, autonomously controlling the instrument 22 based on the calculated characteristic may include applying the calculated characteristic in a simulation program. The simulation program may model the movement of the instrument 22, and more specifically, the energy applicator 34, in relationship to the anatomy during the surgical procedure. In one embodiment, the simulation models a bone milling procedure.

It should be appreciated that one of ordinary skill in the art may find uses for autonomously controlling the instrument 22 based on the calculated characteristic other than those described in the above embodiments without departing from the scope of the method.

Figure 4:
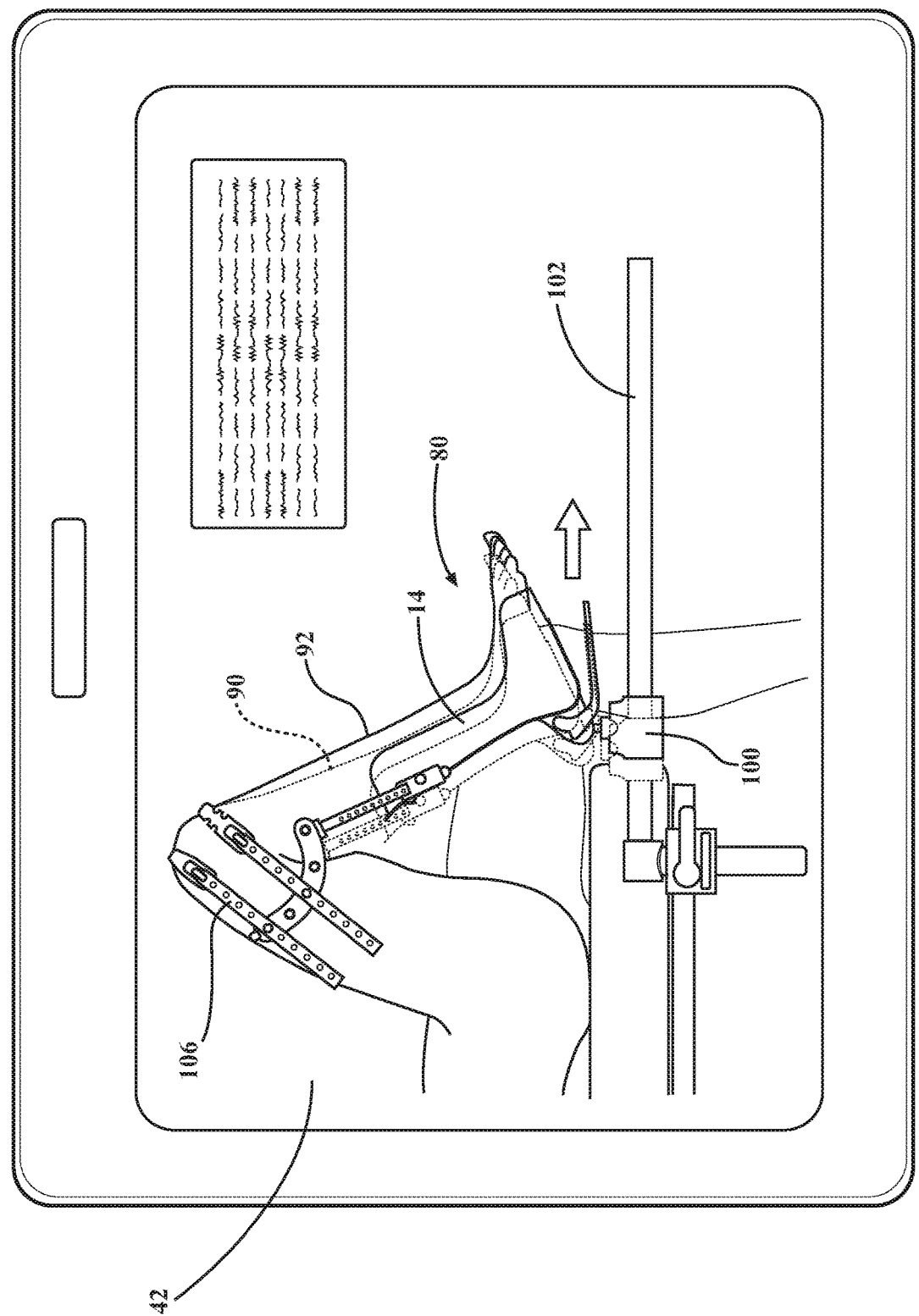
FIG. 4 is a view of a display showing a notification suggesting movement of the anatomy according to one embodiment.
Figure 5:
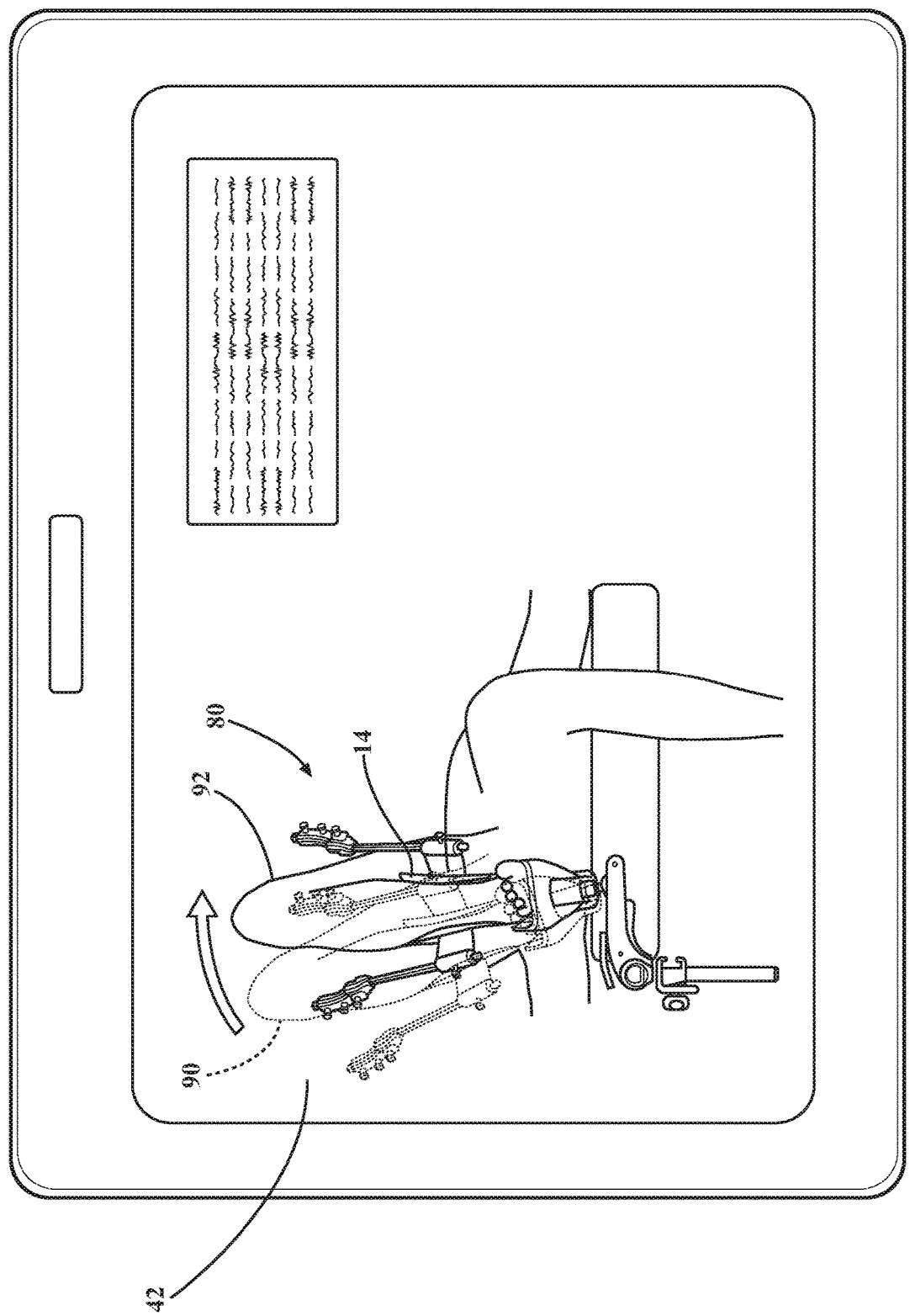
FIG. 5 is a view of the display showing the notification suggesting movement of the anatomy according to another embodiment.

Based on the calculated characteristic, the robotic system 10 may provide a message or notification 80, as shown in FIGS. 4 and 5. The notification 80 aides the medical personnel during the surgical procedure. The notification 80 may be provided on any suitable medium, such as the user interface. In FIGS. 4 and 5, the notification 80 is provided on the display 42 of the navigation system 32. The notification 80 may be provided by images, text, or a combination of images and text. Additionally, the notification 80 may be animated.

The notification 80 is provided based on the calculated characteristic. In one embodiment, the notification 80 is provided based on an assessment of the calculated characteristic. For example, the notification 80 may be provided based on a comparison of the calculated characteristic to a threshold related to optimal operation. The threshold may be a minimum threshold or a maximum threshold. If the calculated characteristic is above the maximum threshold or below the minimum threshold, the robotic system 10 provides the notification 80. For example, a minimum threshold for the stiffness k (or a combination of parameters m, b, and k) may be determined. If the calculated stiffness is below the minimum threshold for the stiffness k, the robotic system 10 provides the notification 80 to the medical personnel that the procedure cannot continue until the anatomy is more securely fastened.

Alternatively or additionally, based on the calculated characteristic, the feed rate in the autonomous or semi-autonomous mode may be adjusted to a level needed to maintain machining accuracy. In one example, the feed rate is decreased until or unless the anatomy is more firmly secured. Specifically, the feed rate may be decreased until or unless the anatomy is more firmly secured in degrees-of-freedom exhibiting low stiffness. Adjustment of the feed rate may be automatic and passive such that medical personnel need not manually adjust the feed rate. Rather, the stiffness of the anatomy is adjusted if faster machining is desired. The robotic system 10 may thereafter display the notification 80 to the medical personnel that the feed rate may be increased if the anatomy is more securely fastened.

In other embodiments, the calculated characteristic is compared against a predetermined range of characteristics for optimal operation. If the calculated characteristic falls outside the range then the robotic system 10 may send the notification 80. For example, if the robotic system 10 determines the calculated characteristic, such as the stiffness characteristic (k), falls outside the range for optimal operation, then the robotic system 10 may send the notification 80 warning the medical personnel of that the calculated characteristic has fallen outside the range or that the surgical procedure should be halted. On the other hand, if the stiffness characteristic (k) falls within the range of optimal operating characteristics and the robotic system 10 may notify the medical personnel that the surgical procedure may continue. Additionally, the aforementioned embodiment may be realized during a calibration procedure. For example, the calibration procedure may terminate when the calculated characteristic falls within the range of optimal operating characteristics.

In many instances, it is advantageous to provide the notification 80 with instructions on how to adjust the anatomy of the patient based on the calculated characteristic. The notification 80 may alert the medical personnel to reposition the anatomy in the surgical holder 14 such that the anatomy is more securely fastened. Repositioning of the anatomy is carried out by manipulating the surgical holder 14. As such, the notification 80 may suggest instructions on how to manipulate (e.g., move/adjust) the surgical holder 14. The position of the anatomy can be adjustably set along a plurality of degrees of freedom using the surgical holder 14. The force applied to the anatomy generates the response by the anatomy with respect to each degree of freedom. For each degree of freedom, the response of the anatomy is measured. The calculated characteristic is determined for each degree of freedom. Based on the calculated characteristic, a determination can be made as to whether the anatomy should be adjusted with respect to any of the degrees of freedom. The determination can be made according to various methods, including whether the calculated characteristic has exceed a predetermined threshold or a range. The magnitude or extent of the adjustment may also be determined.

The notification 80 provides suggestions that are derived from calculations based on the degrees of freedom of the anatomy. By determining which degrees of freedom of the anatomy require manipulation and the extent of such manipulation, the notification 80 provides suggestions to modify the position of the surgical holder 14. By modifying the position of the surgical holder 14, the position of the anatomy changes. The calculated characteristic changes as the position of the anatomy changes. As such, the notification 80 promotes repositioning of the anatomy to change the calculated characteristic.

As shown in FIGS. 4 and 5, the notification 80 may be displayed as an image or animation visually showing how to adjust the surgical holder 14. The notification 80 indicates how to move the anatomy from a current position 90 to a suggested position 92. The current position 90 of the anatomy is the real-time position of the anatomy. The suggested position 92 is derived from the calculated characteristic, as described above. In FIGS. 4 and 5, the current position 90 is illustrated by dashed lines and the suggested position 92 is illustrated by solid lines.

Suggestions provided by the notification 80 may depend on the configuration of the surgical holder 14. In FIGS. 4 and 5, for example, the anatomy supported by the surgical holder 14 is a limb, such as a leg. The surgical holder 14 includes mechanisms for extending or flexing the anatomy. The surgical holder 14 is supported by a sled 100, which moves along a support bar 102. The notification 80 may suggest unlocking the sled 100 from the support bar 102 and moving the sled 100 along the support bar 102 to the suggested position 92. The surgical holder 14 is then locked in the suggested position 92. The direction of the suggested movement of the sled 100 in FIG. 4 is illustrated by an arrow for simplicity. The notification 80 may suggest movement of the leg from extension to flexion, or vice-versa. The notification 80 suggests movement of the anatomy along any given degree(s) of freedom. For example, in FIG. 5, the notification 80 suggests rotating the surgical holder 14 medially (toward centerline of the patient). Alternatively, the notification 80 may suggest rotating the surgical holder 14 laterally (away from the centerline of the patient). In such instances, the notification 80 may suggest to move the surgical holder 14 laterally or medially. Furthermore, as shown in FIG. 4, the surgical holder 14 may include at least one strap 106 for securing the anatomy. The notification 80 may suggest tightening the strap 106.

Of course, the surgical holder 14 may have various other configurations and may be manipulated in various other ways not recited herein. Additionally, the notification 80 may suggest repositioning more than one feature of the surgical holder 14. The notification 80 may also provide instructions through a single step or a series of steps. For example, the notification 80 may first display the suggestion shown in FIG. 4 as a first step and subsequently display the suggestion shown in FIG. 5 as a second step.

In some instances, the notification 80 is passive and merely suggests movement to the suggested position 92. In such instances, the robotic system 10 generally does not determine whether the surgical holder 14 is moved to the suggested position 92. In other instances, the notification 80 is active such that the robotic system 10 determines whether the anatomy and/or the surgical holder 14 have reached the suggested position 92. The robotic system 10 may monitor movement of the anatomy and surgical holder 14 intermittently or continuously. The robotic system 10 may employ any suitable method or system for determining whether the anatomy and surgical holder 14 have reached the suggested position 92. For example, the robotic system 10 may utilize the navigation system 32 and patient trackers 58, 60 for determining the current and suggested positions 92 of the anatomy and/or surgical holder 14.

Additionally, the robotic system 10 may employ any suitable notification method for communicating that the suggested position 92 has been reached. For example, the navigation system 32 may display the current position 90 of the anatomy and/or surgical holder 14 in relation to the suggested position 92 of the anatomy and/or surgical holder 14. As the anatomy and/or surgical holder 14 is moved, the displayed current position 90 of the anatomy and/or surgical holder 14 approaches the displayed suggested position 92. The adjustment is made until the displayed current position 90 reaches the displayed suggested position 92. Of course, other methods of communication, such as haptic or auditory methods, may be employed to communicate that the suggested position 92 has been reached.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical system configured to interact with an anatomy secured by a support, the surgical system comprising:
a robotic manipulator comprising an arm formed of a plurality of links and joints;
an instrument supported by a distal end of the arm of the robotic manipulator; and
one or more controllers coupled to the robotic manipulator and being configured to:
control the robotic manipulator to move the instrument towards the anatomy to apply a force externally to the anatomy;
measure an extent to which the anatomy is secured by the support in response to the force externally applied to the anatomy; and
control the robotic manipulator based on the measured extent.

2. The surgical system of claim 1 wherein the one or more controllers are configured to:
permit the robotic manipulator to continue with a surgical procedure in response to determining that the measured extent satisfies a threshold condition; or
prohibit the robotic manipulator from continuing with a surgical procedure in response to determining that the measured extent does not satisfy a threshold condition.

3. The surgical system of claim 1 wherein the one or more controllers are configured to:
generate a notification to inform that the anatomy is properly secured by the support in response to determining that the measured extent satisfies a threshold condition; or
generate a notification to inform that the anatomy is not properly secured by the support in response to determining that the measured extent does not satisfy a threshold condition.

4. The surgical system of claim 1 wherein the one or more controllers are configured to generate a notification based the measured extent.

5. The surgical system of claim 4 wherein the one or more controllers are configured to generate the notification to suggest how to physically adjust the anatomy from a current position to a suggested position.

6. The surgical system of claim 5 wherein the one or more controllers are configured to:
monitor movement of the anatomy and the support;

determine whether the anatomy and/or the support has reached the suggested position; and generate the notification for communicating that the suggested position has been reached.

7. The surgical system of claim 4 wherein the one or more controllers are configured to generate the notification to suggest at least one of:

how to physically adjust the support based on the measured extent; and tightening a retaining feature of the support.

8. The surgical system of claim 1 wherein the one or more controllers are configured to measure the extent by measuring a difference between an actual position of the instrument relative to the anatomy and an intended position of the instrument relative to the anatomy.

9. The surgical system of claim 1 wherein the one or more controllers are configured to measure the extent by measuring one or more of:

a displacement of the anatomy; and a stiffness of the anatomy.

10. The surgical system of claim 1 further comprising a navigation system configured to track a position of the anatomy and wherein the one or more controllers are configured to measure the extent by evaluating the tracked positions of the anatomy.

11. A method of operating a surgical system configured to interact with an anatomy secured by a support, the surgical system comprising a robotic manipulator comprising an arm formed of a plurality of links and joints, an instrument supported by a distal end of the arm of the robotic manipulator, and one or more controllers coupled to the robotic manipulator, the method comprising the steps of:

controlling, with the one or more controllers, the robotic manipulator to move the instrument towards the anatomy for applying a force externally to the anatomy;

measuring, with the one or more controllers, an extent to which the anatomy is secured by the support in response to applying the force externally to the anatomy; and controlling, with the one or more controllers, the robotic manipulator based on the measured extent.

12. The method of claim 11 wherein controlling, with the one or more controllers, the robotic manipulator based on the measured extent further comprises the one or more controllers:

permitting the robotic manipulator to continue with a surgical procedure in response to determining that the measured extent satisfies a threshold condition; or prohibiting the robotic manipulator from continuing with a surgical procedure in response to determining that the measured extent does not satisfy a threshold condition.

13. The method of claim 11 wherein controlling, with the one or more controllers, the robotic manipulator based on the measured extent further comprises the one or more controllers:

generating a notification to inform that the anatomy is properly secured by the support in response to determining that the measured extent satisfies a threshold condition; or generating a notification to inform that the anatomy is not properly secured by the support in response to determining that the measured extent does not satisfy a threshold condition.

14. The method of claim 11 wherein controlling, with the one or more controllers, the robotic manipulator based on the measured extent further comprises the one or more controllers generating a notification based the measured extent.

15. The method of claim 14 further comprising the one or more controllers generating the notification to suggest how to physically adjust the anatomy from a current position to a suggested position.

16. The method of claim 11 further comprising the one or more controllers measuring the extent by measuring a difference between an actual position of the instrument relative to the anatomy and an intended position of the instrument relative to the anatomy.

17. The method of claim 11 further comprising the one or more controllers measuring the extent by measuring one or more of:

a displacement of the anatomy; and a stiffness of the anatomy.

18. The method of claim 11 further comprising a navigation system configured to track a position of the anatomy and further comprising the one or more controllers measuring the extent by evaluating the tracked positions of the anatomy.

19. The method of claim 11 wherein controlling, with the one or more controllers, the robotic manipulator based on the measured extent is further defined by controlling the instrument to account for the extent to which the anatomy is secured by the support.

* * * * *